United States Patent [19]

Vezértnée Sólyom et al.

[11] Patent Number: 4,755,510

[45] Date of Patent: Jul. 5, 1988

[54] NOVEL ANTICONVULSIVE TETRAHYDRO-1,2,4-OXADIAZINE-5-THION DERIVATIVES AND USE

[75] Inventors: Csilla Vezértnée Sólyom; László Ürögdi; Lajos Kisfaludy; László Otvös; Zsuzsanna Tegyey; Helga Tüdös née Feuer; Éva Pálosi; Sára Rónai née Lukács; Eszter Cholnoky; László Szporny, all of Budapest, Hungary

[73] Assignees: Richter Gedeon Vegyeszeti Gyar R.T.; MTA Kozponti Kemiai Kutatointezete, both of Budapest, Hungary

[21] Appl. No.: 786,203

[22] Filed: Oct. 10, 1985

[30] Foreign Application Priority Data

Oct. 11, 1984 [HU] Hungary ............................. 3809/84

[51] Int. Cl.[4] .................. A61K 31/535; C07D 273/04
[52] U.S. Cl. ..................................... 514/229.2; 544/66
[58] Field of Search ........................... 544/66; 514/228

[56] References Cited

U.S. PATENT DOCUMENTS 4,371,534  1/1983  Ürodgi et al. ................... 544/68 X Primary Examiner—Richard L. Raymond
Attorney, Agent, or Firm—Karl F. Ross; Herbert Dubno; Jonathan Myers

[57] ABSTRACT

The present invention relates to novel optically active or racemic tetrahydro-1,2,4-oxadiazine-5-thione derivatives of the formula

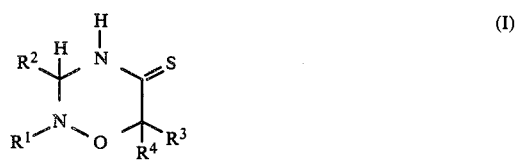

methods for their preparation, pharmaceutical compositions comprising the said compounds as active ingredients and a method for the anticonvulsive treatment of mammals, especially human beings.

The compounds of the formula I have as good activity as diphenyl hydantoine but their toxicity is much lower.

6 Claims, No Drawings

NOVEL ANTICONVULSIVE TETRAHYDRO-1,2,4-OXADIAZINE-5-THION DERIVATIVES AND USE

The present invention relates to novel optically active and racemic tetrahydro-1,2,4-oxadiazine-5-thion derivatives of the formula

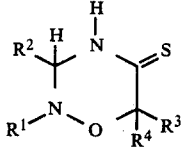  (I)

processes for preparing the same, anticonvulsive pharmaceutical compositions comprising the same and their use in therapy.

In the formula (I)

$R^1$ stands for benzyloxycarbonyl, alkanoyl having 1 to 5 carbon atoms, thioalkanoyl having 1 to 5 carbon atoms, benzoyl which can be substituted with one or more alkyl having 1 to 4 carbon atoms or alkoxy having 1 to 4 carbon atoms, alkylcarbamoyl having 1 to 4 carbon atoms in the alkyl moiety or alkylsulphonyl having 1 to 4 carbon atoms, $R^2$ is phenyl or naphthyl which can be substituted with one or more alkyl having 1 to 4 carbon atoms, alkoxy having 1 to 4 carbon atoms or amino disubstituted with the same or different alkyl groups having 1 to 4 carbon atoms, $R^3$ is hydrogen, alkyl having 1 to 8 carbon atoms or benzyl, and $R^4$ is hydrogen or alkyl having 1 to 4 carbon atoms.

The tetrahydro-1,2,4-oxadiazine-5-thion derivatives have not been described in the prior art.

BACKGROUND OF THE INVENTION

Analogous oxo-compounds have been disclosed in Hungarian patent specification No. 181,586. The pharmaceutical activity of these compounds is similar to that of the compounds of the invention, but as an undesired side-effect, they posses neurotoxic effects as well. The target compounds of the present invention do not show any similar side-effect.

SPECIFIC DESCRIPTION

The compounds of the formula (I) can be prepared by (a) reacting an optically active or racemic tetrahydro-1,2,4-oxadiazine-5-one derivative of the formula

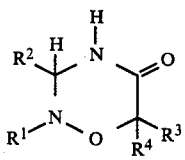  (II)

wherein $R^1$, $R^2$, $R^3$ and $R^4$ are the same as defined hereinabove—with phosphorous pentasulfide in an aprotic medium, or (b) reacting an optically active or racemic alpha-aminooxythiocarboxyclic amide of the formula

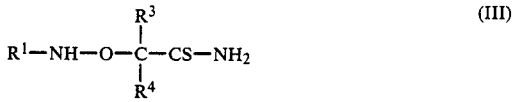  (III)

wherein $R^1$, $R^3$ and $R^4$ are the same as defined hereinabove, with an aldehyde of the formula

  (IV)

wherein $R^2$ is the same as defined hereinabove.

The compounds of the formula (II) are known; they can be prepared according to the process of Hungarian patent specification No. 181,586.

In process variant (a) hydrocarbons, especially aromatic hydrocarbons, e.g. benzene, toluene, xylene can preferably be used as protic media. The reaction is carried out preferably at the boiling point of the solvent within 0.5 to 24 hours.

The progress of the reaction can be controlled by thin-layer chromatography. As the reaction is finished, the suspension is filtered off and the solution is evaporated. The residual oil can be purified e.g. by recrystallization or column chromatography.

In the process according to process variant (b) preferably a mixture of acetic acid and acetic anhydride supplemented with some mineral acid is used as reaction medium. The condensation is carried out under similar conditions that are described by Hungarian patent specification No. 181,586. The reaction can be carried out at room (15° to 22° C.) temperature within 1 to 2 hours.

The progress of the reaction is preferably controlled by thin-layer chromatography. When the reaction is finished, the reaction mixture is evaporated, the residue is dissolved in a water non-miscible solvent, washed to neutral with water and evaporated to dryness after drying. The endproduct can be purified similarly to the preceding procedure by recrystallization or column chromatography.

The novel compounds of the formula (III) can be prepared from the alpha-aminooxy carboxylic amides of the formula

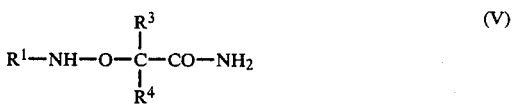  (V)

in any manner known from the prior art [J. Zabicky: "The Chemistry of Amides", Interscience Publishers, a division of Wiley and Sons, London-New-York-Sydney-Toronto (1970) and the other publications cited therein] e.g. by preparing a nitrile of the formula

  (VI)

wherein $R^1$, $R^3$, $R^4$ are the same as defined hereinabove, from the corresponding acid amide in an aprotic solvent, preferably pyridine in a reaction with phosphorous oxychloride, and obtaining the thioamide of the formula (III) after coupling hydrogen sulfide in an aprotic solvent (pyridine).

The alpha-aminooxy-carboxylic amides of the formula (V) are known compounds [Mh. Chem., 92, 725. (1961); Helv. Chim. Acta., 1969, 569, Il. Farm. Ed. Sci., 31(3), 169 (1976)].

In the compounds of the formula (I) wherein $R^3$ and $R^4$ are different, the carbon atom in position 6 is of asymmetric configuration, therefore these compounds can exist in optically active or racemic forms. The present invention relates to both the racemic and optically active forms of the compounds of the formula (I) having an asymmetric carbon atom in position 6.

The optically active compounds of the formula (I) can be prepared e.g. by using the optically active derivative of the compounds of the formula (II) or (III) having an asymmetric carbon atom in position 6 as starting material.

Preferred compounds within the formula (I) are those having the formulas wherein $R^1$ is alkanoyl having 1 to 4 carbon atoms,
$R^2$ is phenyl optionally substituted with alkyl having 1 to 4 carbon atoms or amino disubstituted with alkyl having 1 to 4 carbon atoms,
$R^3$ is hydrogen or alkyl having 1 to 4 carbon atoms,
$R^4$ stands for hydrogen.

Particularly preferred compounds of the formula (I) are wherein $R^1$ represents acetyl,
$R^2$ stands for phenyl, tolyl or dimethylamino phenyl,
$R^3$ is hydrogen, methyl or ethyl and
$R^4$ stands for hydrogen.

The most preferred compound is 2-acetyl-3-o-tolyl-6-methyl-tetrahydro-1,2,4-oxadiazine-5-thion.

The anticonvulsive activity, neurotoxicity as well as the acute toxicity of the compounds of the invention were examined in the usual animal tests.

The compound to be tested was suspended in 2 percent aqueous Tween 80 (polyoxyethylene sorbitane monolaurate) solution and it was orally administered to the animals through a bougie in a dose of 30 mg/kg when the anticonvulsive activity was tested, while in a dose of 120 mg/kg when the neurotoxic activity was examined. The effect triggered was measured after 1 hour of the administration. Male CFLP (LATI) mice having a weight of 18 to 22 g were used in the tests.

1. Examination of the anticonvulsive activity (a) Maximal electroshock (MES)

The animals were shocked with a corneal electrode (20 mA, 0.2 sec.) (H. Schachs Elektronik, Marchs, Augstatten, Germany, "schockreizgerat" typ. 207) according to the method of E. A. Swinyard et al. (J. Pharmacol. Exp. Ther. 106, 318 (1952)]. 100% of the control animals responded to the stimulus by the tonic extensoric spasm of the lower limbs. The lack of these occurences was attributed to the protection obtained by the treatment.

(b) Spasm stimulated by Pentetrazole (PTT)

According to the method of G. M. Everett and R. K. Richard [J. Pharmacol. Exp. Ther., 81, 402, (1944)] the test animals were treated with 125 mg/kg of Pentetrazole (pentamethylene tetrazole) after 1 hour of the administration of the compound to be tested. The lack of the clonic spasm (KI) and the tonic extensoric spasm of the lower limbs (TE) was attributed to the protection obtained as a result of the treatment.

(c) Spasm stimulated by strychnine (STr)

According to the method of T. L. Kerley et al. [J. Pharmacol. Exp. Ther. 132, 360 (1961)] the test animals were i. p. treated with 2.5 mg/kg of strychnine after 1 hour of the administration of the active ingredient to be tested. Those animals were considered to be protected which, as a result of the treatment, did not suffer from spasms.

2. Examination of the neurotoxicity (measure of the muscle uncoordination) (FR)

The change of the coordinated muscle motion was examined on a rotating bar according to the method of C. J. Carr [J. Pharmacol. Exp. Ther., 121, 354 (1957)] (diameter: 20 mm, number of revolutions: 12/minute). The trained control animals could stay on the bar for 120 seconds. After 1 hour of the administration of the test compound, it was examined which percent of the animals fell down from the rotating bar within 120 seconds.

3. Acute toxicity

The toxicity of the compounds was examined after the administration of 1000 mg/kg of the test compound in one dose by an observation through 14 days. The $LD_{50}$ value (50 percentile lethal dose) was calculated by probite analysis on the basis of the percentile ratio of the animals died within the 14 days.

As control compounds diphenyl hydantion and 2-acetyl-3-phenyl-(tetrahydro-1,2,4-oxadiazine-5-one) (Hungarian patent specification No. 181,568) were used. The results are summarized in Table I.

TABLE I

| Active ingredient | Anticonvulsive activity | | | | Neuro. tox. | Acute tox. $LD_{50}$ |
| | MES | PTT | | | FR | mg/kg |
| | | KI | TE | Str | | p.o. |
| | $ED_{50}$ mg/kg p.o. | | | | | |
|---|---|---|---|---|---|---|
| A | 11.9 | 0 | 6.1 | 0 | 0 | 1000 |
| B | 16.1 | 0 | 12.6 | 0 | 0 | 1000 |
| C | 10.0 | 0 | 4.3 | 25.6 | 0 | 1000 |
| D | 30.0 | 0 | 9.9 | 0 | 0 | 1000 |
| E | 10* | 0 | 16.6 | 0 | 0 | 1000 |
| F | 40* | 0 | 15.4 | 0 | 0 | 1000 |
| K1 | 8.3 | 0 | 9.9 | 0 | 47.7 | 278 |
| K2 | 22.7 | 0 | 13.4 | 0 | 130.0 | 1188 |

The symbols given in the column of the active ingredient represent the following compounds:

| Compound | $R^1$ | $R^2$ | $R^3$ | $R^4$ | Configuration | |
| | | | | | C(6) | C(3)–C(6) |
|---|---|---|---|---|---|---|
| A | $CH_3$—CO— | $C_6H_5$— | $CH_3$— | H— | R,S | cis |
| B | $CH_3$—CO— | $C_6H_5$— | $CH_3$— | H— | R | cis |
| C | $CH_3$—CO— | o-Tolyl- | $CH_3$— | H— | R,S | cis |
| D | $CH_3$—CO— | p-Dimethyl-amino-phenyl | $CH_3$— | H— | R,S | cis |
| E | $CH_3$—CO— | $C_6H_5$— | H— | H— | — | — |
| F | $CH_3$—CO— | $C_6H_5$— | $C_2H_5$— | H— | R,S | cis |

K1 (control): Diphenyl hydantoin
K2 (control): 2-Acetyl-3-phenyl-tetrahydro-1,2,4-oxadiazine-5-one xinhibition (%) due to 30 mg/kg of active ingredient (p.o.)
MES: maximal electroshock
PTT: inhibition of the spasm stimulated by pentetrazole
KL: chlonic spasm
TE: tonic extensoric spasm
Str: inhibition of the spasm stimulated by strychnine
FR: rotating bar It is demonstrated by the data of the above table that the compounds of the formula (I) possess significant anticonvulsive activity, their protection against the tonic extensoric spasms of the lower limbs—caused by maximal electroshock and Pentetrazole—is in the same order as that of diphenyl hydantoin. After administration of the active ingredient in one dose, the effect can be observed very soon and the action is long-lasting; the $ED_{50}$ values of the active ingredients measured after 0.5 to 6 hours of the administration are practically the same. Neurotoxic symptoms cannot be observed when a dose of 120 mg/kg is administered, their lack of toxicity is very favorable, therefore they can be much more widely used in therapy than the known compounds with similar action. The quality of their pharmaceutical effect is the same as that of diphenyl hydantoin, therefore they are can preferable used in accessions of grandmal type. They can be more preferably used in therapy than diphenyl hydantoin due to their lower toxicity.

The compounds of the present invention can be administered in the form of usual pharmaceutical formulations.

The dosage administered will, of course, vary depending on known factors such as the pharmacodynamic characteristics of the particular agent, and its mode and route of administration; age, health and weight of the recipient; nature and extent of symptoms, kind of concurrent treatment, frequency of treatment, and the effect desired. Usually a daily dosage of active ingredient can be about 5 to 15 mg/kg of body weight, and preferably 5 to 7.5 milligrams per kilogram per day, preferably given in divided doses 2 to 4 times a day or in sustained release form.

Dosage forms (compositions) suitable for internal administration contain from about 1.0 milligram to about 500 milligrams of active ingredient per unit. In these pharmaceutical compositions the active ingredient will ordinarily be present in an amount of about 0.5 to 95% by weight based on the total weight of the composition.

The active ingredient can be administered orally in solid dosage forms, such as capsules, tablets, and powders, or in liquid dosage forms, such as elixirs, syrups, and suspensions, it can also be administered parenterally, in sterile liquid dosage forms or enterally. The dosage forms comprise one or more pharmaceutically acceptable carriers and/or diluents and/or excipients besides the active ingredient. Suitable pharmaceutical carriers are described in Remington's Pharmaceutical Sciences, A. Osol, a standard reference text in this field.

The invention is illustrated by the following, non-limiting examples. The abbreviations used in the Examples are in accordance with the IUPAC prescriptions.

The melting points of the compounds prepared according to the examples were determined in a dr. Tottoli-type (Büchi) equipment. The thin-layer chromatograms were prepared on a "Kieselgel G" (Merck) silica gel layer being sensitive to ultraviolet light prepared according to the method of Stahl. The following solvent mixtures were used for the development of the chromatograms:
A=chloroform:methanol=80:1 (by volume)
B=chloroform
C=benzene:acetone=1:1 (by volume).

In most cases the detection of the thin-layer chromatograms was carried out by applying one or more from the following methods:
1. Radiation with ultra violet light having a wave length of 254 nm
2. Treatment with iodine vapors
3. Spraying with a mixture of tolidine/potassium iodide after treating with chlorine gas The structure of the compounds prepared was verified with elemental analysis and on the basis of their infra red (IR) and NMR spectras. The IR spectras were measured in an apparatus of "Perkin-Elmer 257" type, while the NMR spectras were measured in an apparatus of "Varian EM-60" type.

The reaction mixtures were evaporated in vacuo in a "Rotavapor R" (Büchi) evaporator at a temperature below 50° C.

In the course of the measuring of the NMR spectras if a non-miscible solvent, e.g. deuterochloroform had been used, the spectra were also taken after an extraction with heavy water (deuterium oxide) when the signs of the protons being able to be easily changed to deuterium disappeared. (This is indicated in the text with the symbol "x").

EXAMPLE 1

2-Acetyl-3-(2-methylphenyl)-6-methyl-tetrahydro-1,2,4-oxadiazine-5-thion 4.96 g (20 millimoles) of 2-acetyl-3-(2-methylphenyl)-6-methyl-tetrahydro-1,2,4-oxadiazine-5-thion are vigorously stirred with 4.5 g (20 millimoles) of phosphorous pentasulphide in 100 ml of dry benzene under boiling until the starting material cannot be detected by thin-layer chromatographic examination. This is 50 minutes in this case. The hot reaction mixture is clarified with charcoal, filtered and evaporated. The residual oil is dissolved in 45 ml of ethanol, clarified with charcoal and filtered off. The product is crystallized at a temperature of +5° C. The precipitating crystalls are filtered off. 2.6 g of crystalline product are obtained. Yield: 49%. Melting point: 167°–170° C.

The 2.6 g of thione are purified by chromatography on a column filled with 140 g of Merck Kieselgel 60 (70–230 mesh) using an eluent consisting of a 80:1 mixture of chloroform and methanol. 1.85 g of pure title product are obtained.

| Elemental analysis ($C_{13}H_{16}N_2O_2S$) (M: 264.34) | | | | |
|---|---|---|---|---|
| | C | H | N | S |
| Calculated: | 59.06 | 6.1 | 10.59 | 12.12%; |
| Found: | 58.92 | 6.14 | 10.38 | 11.95%. |
| IR (KBr) cm$^{-1}$: | 3200 (NH) | | 1645 (C=O) | |
| | 1530 (thioamide) | | 770 (aromatic) | |
| $^1$H—NMR (CDCl$_3$) (ppm): 1.72 d (CH—$\underline{CH_3}$) 2.12 s (—CO—$\underline{CH_3}$) | | | | |
| 2.64 s (Ar—$\underline{CH_3}$), 4.68 q ($\underline{CH}$—CH$_3$) 6.8 s ($\underline{CH}$—Ar) | | | | |
| 7.3 m (4H, aromatic) 9.2 b$^x$ (NH). | | | | |

EXAMPLES 2 TO 21

The compounds of the formula I listed in Table 2 are prepared according to the method of Example 1.

TABLE 2

| R¹ | R² | R³ | R⁴ | Mp. (°C.) | $[\alpha]_d^{20}$ c = 1 DMF | $R_f$ | Reaction time (min) | Yield (%) | Purification |
|---|---|---|---|---|---|---|---|---|---|
| benzyloxy-carbonyl | Ph— | H— | H— | 123–124 | — | 0.62/A | 1440 | 52 | 1 |
| Ac— | Ph— | H— | H— | 172–174 | — | 0.43/A | 150 | 45 | 2 |
| Ac— | Ph— | Me— | H— | 175–179 | — | 0.33/A | 210 | 20 | 1 |
| Ac— | Ph— | Me— | H— | 201–203 | +107.7 | 0.46/A | 45 | 35 | 2 |
| Ac— | Ph— | Me— | H— | 200–202 | −100.0 | 0.46/A | 45 | 38 | 2 |
| Ac— | Ph— | Et— | H— | 121–123 | — | 0.43/A | 50 | 27 | 2 |
| Ac— | Ph— | n-octyl— | H— | 107–109 | — | 0.51/A | 60 | 27 | 2 |
| Ac— | Ph— | Me— | Me— | 172–174 | — | 0.35/A | 240 | 41 | 2 |
| Ac— | Ph— | Bzl— | H— | oil | +218.0 | 0.62/A | 25 | 21 | 2 |
| Ac— | 1-napthyl | Me— | H— | 214–215 | — | 0.79/A | 80 | 36 | 2 |
| Ac— | 4-Me₂N—Ph— | Me— | H— | 183–184 | — | 0.28/A | 60 | 10.9 | 2 |
| Ac— | 4-MeO—Ph | Me— | H— | 104–105 | — | 0.28/A | 15 | 11.4 | 2 |
| thioacetyl | Ph— | H— | H— | 199–200 | — | 0.71/A | 1440 | 15 | 1 |
| EtCO— | Ph— | H— | H— | 150–152 | — | 0.35/A | 120 | 32 | 2 |
| benzoyl- | Ph— | H— | H— | 163–165 | — | 0.27/B | 25 | 40.4 | 1 |
| benzoyl- | Ph— | Me— | H— | 162–163 | — | 0.33/B | 30 | 16 | 1 |
| MeSO₂— | Ph— | H— | H— | 168–169 | — | 0.28/B | 20 | 17 | 2 |
| MeSO₂— | Ph— | Me— | H— | 189–190 | — | 0.31/B | 30 | 34.7 | 2 |
| MeNHCO— | Ph— | H— | H— | 193–195 | — | 0.1/B | 25 | 13.8 | 1 |
| MeNHCO— | Ph— | Me— | H— | 186–188 | — | 0.1/B | 20 | 14.8 | 1 |

Remarks:
A = a 80:1 mixture of chloroform and methanol
B = chloroform
1 = recrystallization from ethanol
2 = column chromatography; eluent: a 80:1 mixture of chloroform and methanol

EXAMPLE 22

2-Acetyl-3-phenyl-tetrahydro-1,2,4-oxadiazine-5-thion

I. Alpha-(acetyl-aminooxy)-thioacetamide 19.82 g (150 millimoles) of alpha-(acetylaminooxy)-acetamide were dissolved in 100 ml of pyridine under vigorous stirring. A mixture of 24.53 g (160 millimoles) of phosphorous oxychloride and 25 ml of dichloromethane are added dropwise to this solution at a temperature of −5° C. and the solution is stirred at a temperature of 0° C. for 1.5 hours. The dichloromethan solution is dryed over anhydrous sodium sulphate and evaporated.

The 15 g of oil thus obtained are dissolved in 15 ml of pyridine, 18.1 ml (131 millimols) of triethyl amine are added and H₂S is led into the solution for 2 hours. The end of the reaction is controlled by thin-layer chromatography. After the disappearance of the starting nitrile, the solution is evaporated, the residual oil is dissolved in 200 ml of ethyl acetate and extracted with 3×100 ml of water. The residue is crystallized from a mixture of ethyl acetate and ether at a temperature of +5° C.

11 g (49.5%) of crystalline title product are obtained. Melting point: 136°–138° C. $R_f$=0.38 (C).

| Elemental analysis (C₄H₈N₂O₂S) (M = 148.18) | | | |
|---|---|---|---|
| | C | H | N | S |
| calculated | 32.44 | 5.44 | 18.9 | 21.63%; |
| found: | 32.35 | 5.58 | 19.06 | 21.47%. |
| IR (KBr) cm⁻¹: | 1650 (C=O) 1270 (C=S) 3280, 3130 (NH) 1540 (Amide II) | | | |

II. 2-Acetyl-3-phenyl-tetrahydro-1,2,4-oxadiazine-5-thion 1.48 g (10 millimoles) of alpha-(acetylaminooxy)-thioacetamide are dissolved in a mixture of 10 ml of acetic acid and 1.3 ml of acetic anhydride, thereafter 1.3 ml (13 millimoles) of freshly distilled benzaldehyde and then 0.5 ml of concentrated sulfuric acid are added. The mixture is stirred for 3 hours at room temperature, then 2.8 g of crystalline sodium acetate are added, stirred for 10 minutes, thereafter the solvent is evaporated under vacuum. The residue is dissolved in 30 ml of ethyl acetate, the solution is extracted with 20 ml of water. The organic layer is dried over anhydrous sodium sulfate then evaporated to dryness. The residue is crystallized from ethanol at a temperature of +5° C. 1.25 g (52.9%) of crystalline title product are obtained. M.p.: 172°–174° C. $R_f$(A)=0.43.

| Elemental analysis (C₁₁H₁₂N₂O₂S) (M = 236.34) | | | |
|---|---|---|---|
| | C | H | N | S |
| Calculated: | 56.15 | 5.1 | 11.9 | 13.63%; |
| Found: | 56.3 | 5.2 | 11.9 | 13.62%. |
| IR (KBr) cm⁻¹: | 3220 (NH) 1655 (C=O) 1525 (thioamide) 1585,740,702 (aromatic) | | | |

¹H—NMR(polysol) (ppm): 2.13 s (—CO—CH₃) 4.83 sd,$\check{s}$-CH₂—)
6.61 s (CH—Ar) 7.36 s (aromatic) 10.6 b$^x$ (—NH—)

Hungarian patent specification No. 181,586 referred to in the text corresponds to Belgian patent specification No. 891,652.

We claim:

1. An optically active or racemic tetrahydro-1,2,4-oxadiazine-5-thion of the formula

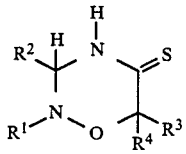

(I)

wherein
R¹ stands for benzyloxycarbonyl, alkanoyl having 1 to 5 carbon atoms, thioalkanoyl having 1 to 5 carbon atoms, benzoyl which can be substituted with one or more alkyl having 1 to 4 carbon atoms or alkoxy having 1 to 4 carbon atoms, alkylcarbamoyl having 1 to 4 carbon atoms in the alkyl moiety or alkylsulphonyl having 1 to 4 carbon atoms,
R² is phenyl or naphthyl which can be substituted with one or more alkyl having 1 to 4 carbon atoms, alkoxy having 1 to 4 carbon atoms or amino disubstituted with the same or different alkyl groups having 1 to 4 carbon atoms,
$R^3$ is hydrogen, alkyl having 1 to 8 carbon atoms or benzyl, and
$R^4$ is hydrogen or alkyl having 1 to 4 carbon atoms.

2. The compound defined in claim 1 wherein
$R^1$ is alkanoyl having 1 to 4 carbon atoms,
$R^2$ is phenyl which can be substituted with alkyl having 1 to 4 carbon atoms or amino disubstituted by the same or different alkyl groups having 1 to 4 carbon atoms,
$R^3$ is hydrogen or alkyl having 1 to 4 carbon atoms,
$R^4$ is hydrogen.

3. The compound defined in claim 1 wherein
$R^1$ stands for acetyl,
$R^2$ stands for phenyl, tolyl or dimethylamino phenyl,
$R^3$ stands for hydrogen, methyl or ethyl and
$R^4$ stands for hydrogen.

4. 2-acetyl-3-tolyl-6-methyl-tetrahydro-1,2,4-oxadiazine-5-thion.

5. Pharmaceutical composition affecting the central nervous system, which comprises a racemic or optically active compound of the formula (I) as defined in claim 1, with pharmaceutically acceptable carriers, excipients or diluents.

6. A method for the anticonvulsive treatment of a susceptible animal subject which comprises administering a therapeutically effective dose of an optically active or racemic tetrahydro-1,2,4-oxadiazine-5-thione of the formula (I) as defined in claim 1.

* * * * *